United States Patent
Leem et al.

(10) Patent No.: US 9,490,442 B2
(45) Date of Patent: Nov. 8, 2016

(54) ORGANIC PHOTOELECTRONIC DEVICE AND IMAGE SENSOR

(71) Applicant: Samsung Electronics Co., Ltd., Suwon-Si, Gyeonggi-Do (KR)

(72) Inventors: Dong-Seok Leem, Hwaseong-si (KR); Kwang Hee Lee, Yongin-si (KR); Gae Hwang Lee, Seongnam-si (KR); Yong Wan Jin, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 17 days.

(21) Appl. No.: 14/532,367

(22) Filed: Nov. 4, 2014

(65) Prior Publication Data
US 2015/0287946 A1    Oct. 8, 2015

(30) Foreign Application Priority Data
Apr. 4, 2014   (KR) ................ 10-2014-0040604

(51) Int. Cl.
*H01L 29/08*   (2006.01)
*H01L 35/24*   (2006.01)
(Continued)

(52) U.S. Cl.
CPC ............. *H01L 51/447* (2013.01); *C07F 5/02* (2013.01); *C07F 5/022* (2013.01); *C09B 47/04* (2013.01); *H01L 27/307* (2013.01); *H01L 51/008* (2013.01); *H01L 51/0078* (2013.01);
(Continued)

(58) Field of Classification Search
CPC ............. H01L 51/447; H01L 27/307; H01L 51/0078; H01L 51/008; C07F 5/02; C07F 5/022; C09B 47/04
See application file for complete search history.

(56) References Cited

U.S. PATENT DOCUMENTS 5,679,430 A   10/1997   Shinkai et al.
5,776,656 A   7/1998    Shinkai et al.
(Continued)

FOREIGN PATENT DOCUMENTS

JP   3041230 B2   5/2000
JP   3341394 B2   11/2002
(Continued)

OTHER PUBLICATIONS

Mutolo, K.L.; Mayo, E.I.; Rand, B.P.; Forrest, S.R.; and Thompson, M.E.; "Enhanced open-circuit voltage in subphthalocyanine/C60 organic photovoltaic cells"; 2006; J.Am.Chem.Soc.; vol. 128, pp. 8108-8109.*
(Continued)

*Primary Examiner* — Stephen W Smoot
*Assistant Examiner* — Vicki B Booker
(74) *Attorney, Agent, or Firm* — Harness, Dickey, & Pierce, P.L.C.

(57) ABSTRACT

An organic photoelectronic device includes an anode and a cathode facing each other, and an organic layer between the anode and the cathode, the organic layer including a compound represented by Chemical Formula 1 as a visible light-absorbing body, and at least one of a hole buffer material having an energy bandgap of greater than or equal to about 2.8 eV and a HOMO level between a work function of the anode and a HOMO level of the compound represented by the Chemical Formula 1, and an electron buffer material having an energy bandgap of greater than or equal to about 2.8 eV and a LUMO level between a work function of the cathode and a LUMO level of the compound represented by the Chemical Formula 1.

20 Claims, 15 Drawing Sheets

(51) Int. Cl.
- *H01L 51/00* (2006.01)
- *H01L 51/44* (2006.01)
- *H01L 27/30* (2006.01)
- *C07F 5/02* (2006.01)
- *C09B 47/04* (2006.01)
- *H01L 51/42* (2006.01)
- *H01L 51/50* (2006.01)

(52) U.S. Cl.
CPC ........ *H01L51/0052* (2013.01); *H01L 51/4246* (2013.01); *H01L 51/4253* (2013.01); *H01L 51/5004* (2013.01); *H01L 51/5012* (2013.01); *H01L 2251/552* (2013.01)

(56) References Cited

U.S. PATENT DOCUMENTS

| | | | |
|---|---|---|---|
| 7,863,605 B2 | 1/2011 | Hayashi | |
| 8,045,772 B2 | 10/2011 | Kosuge et al. | |
| 8,242,493 B2 | 8/2012 | Rand et al. | |
| 8,629,431 B2 | 1/2014 | Etori et al. | |
| 2006/0249202 A1* | 11/2006 | Yoo | B82Y 10/00 136/263 |
| 2007/0272918 A1 | 11/2007 | Rand et al. | |
| 2008/0230123 A1* | 9/2008 | Mitsui | C09B 23/0066 136/263 |
| 2010/0084011 A1 | 4/2010 | Forrest et al. | |
| 2011/0012091 A1 | 1/2011 | Forrest et al. | |
| 2012/0308822 A1 | 12/2012 | Etori et al. | |
| 2013/0206218 A1 | 8/2013 | Holmes et al. | |

FOREIGN PATENT DOCUMENTS

| | | |
|---|---|---|
| JP | 2005-289854 A | 10/2005 |
| JP | 2009-268641 A | 11/2009 |
| JP | 2011-140639 A | 7/2011 |
| KR | 20090042881 A | 5/2009 |
| KR | 20120023629 A | 3/2012 |
| WO | WO-2010036963 A1 | 4/2010 |
| WO | WO-2010/120393 A2 | 10/2010 |
| WO | WO-2011065133 A1 | 6/2011 |

OTHER PUBLICATIONS

Seo, H.; Aihara, S; Watabe, T.; Ohtake, H; Kubota, M.; and Egami, N.; Color Sensors with Three Vertically Stacked Organic Photodetectors; 2007; Japanese Journal of Applied Physics; vol. 46, No. 49; pp. L1240-L1242.*

European Search Report dated Aug. 6, 2015 issued in corresponding European Patent Application No. 14193719.3-1555.

R. Pandey et al. "Efficient Organic Photovoltaic Cells Based on Nanocrystalline Mixtures of Boron Subphthalocyanine Chloride and $C_{60}$", Advanced Functional Materials, 2012, 22, pp. 617-624.

* cited by examiner

ORGANIC PHOTOELECTRONIC DEVICE AND IMAGE SENSOR

CROSS REFERENCE TO RELATED APPLICATION

This application claims priority to and the benefit of Korean Patent Application No. 10-2014-0040604 filed in the Korean Intellectual Property Office on Apr. 4, 2014, the entire contents of which are incorporated herein by reference.

BACKGROUND

1. Field

Example embodiments relate to an organic photoelectronic device and an image sensor including the same.

2. Description of the Related Art

A photoelectronic device converts light into an electrical signal using photoelectronic effects, may include a photodiode and/or a phototransistor, and may be applied to an image sensor, a solar cell, and/or an organic light emitting diode.

An image sensor including a photodiode requires relatively high resolution and thus a relatively small pixel. At present, a silicon photodiode is widely used. However, the silicon photodiode may have a problem of deteriorated sensitivity, because the silicon photodiode has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide an organic photoelectronic device having relatively high photoelectric conversion efficiency and wavelength selectivity.

Example embodiments also provide an image sensor including the organic photoelectronic device.

According to example embodiments, an organic photoelectronic device includes an anode and a cathode facing each other, and an organic layer between the anode and the cathode, the organic layer including a compound represented by the following Chemical Formula 1 as a visible light-absorbing body, and at least one of a hole buffer material having an energy bandgap of greater than or equal to about 2.8 eV and a HOMO level between a work function of the anode and a HOMO level of the compound represented by the following Chemical Formula 1, and an electron buffer material having an energy bandgap of greater than or equal to about 2.8 eV and a LUMO level between a work function of the cathode and a LUMO level of the compound represented by the following Chemical Formula 1.

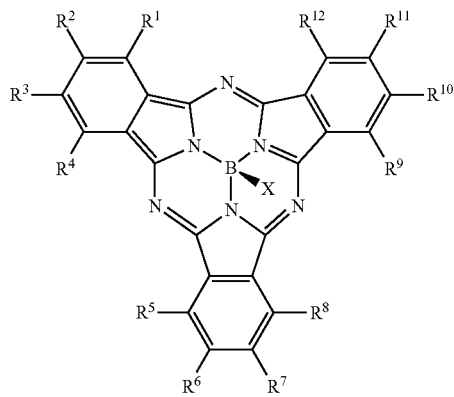

[Chemical Formula 1]

In the above Chemical Formula 1, each of $R^1$ to $R^{12}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen atom, a halogen-containing group, and a combination thereof, and X is an anion.

The hole buffer material and the electron buffer material may not absorb visible light having a wavelength region of about 450 nm to about 800 nm.

The organic layer may further include an active layer including the compound represented by the above Chemical Formula 1 and a charge buffer layer on at least one side of the active layer, the charge buffer layer including at least one of a hole buffer layer including the hole buffer material and an electron buffer layer including the electron buffer material.

The active layer may further include the hole buffer material. The hole buffer material of the active layer may be included in an amount of less than or equal to 50 volume % based on the active layer.

The active layer may further include the electron buffer material. The electron buffer material of the active layer may be included in an amount of less than or equal to 50 volume % based on the active layer.

The organic layer may include an active layer, and the active layer may include the compound represented by the above Chemical Formula 1 and at least one of the hole buffer material and the electron buffer material.

The difference between the HOMO level of the hole buffer material and the HOMO level of the compound represented by the above Chemical Formula 1 may be about 0.01 eV to about 0.89 eV. The HOMO level of the hole buffer material may be greater than about 4.7 eV and less than about 5.6 eV.

The difference between the LUMO level of the electron buffer material and the LUMO level of the compound represented by the above Chemical Formula 1 may be about 0.01 to about 0.89 eV. The LUMO level of the electron buffer material may be greater than about 3.6 eV and less than 4.3 eV.

The compound represented by the above Chemical Formula 1 may be one of compounds represented by the following Chemical Formulae 1a to 1e.

[Chemical Formula 1a]

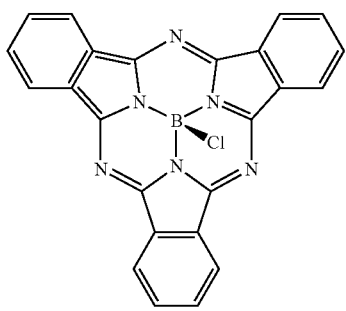

[Chemical Formula 1b]

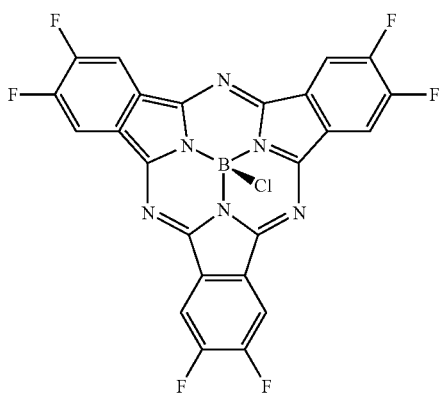

[Chemical Formula 1c]

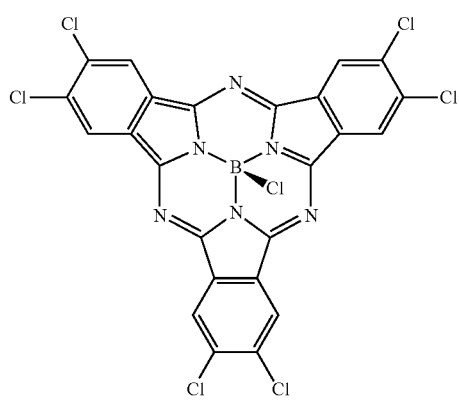

[Chemical Formula 1d]

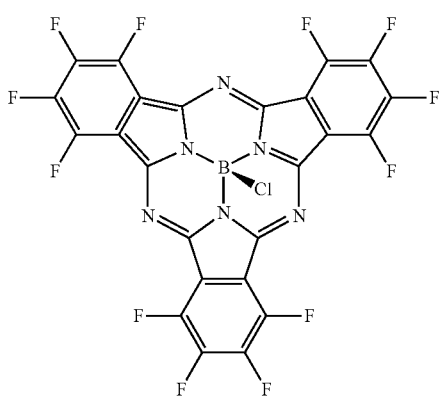

-continued

[Chemical Formula 1e]

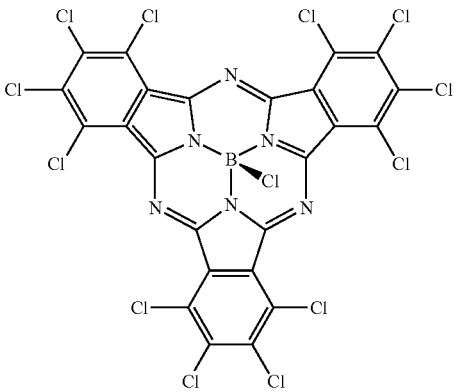

The organic photoelectronic device may selectively absorb light of a green wavelength region. The organic photoelectronic device may have a maximum absorption wavelength ($\lambda_{max}$) at about 500 nm to about 600 nm. The organic photoelectronic device may show a light-absorption curve having a full width at half maximum (FWHM) of about 50 nm to about 150 nm.

According to example embodiments, an image sensor includes the organic photoelectronic device.

The image sensor may include a semiconductor substrate integrated with a plurality of first photo-sensing devices sensing light in a blue wavelength region and a plurality of second photo-sensing devices sensing light in a red wavelength region, a color filter layer on the semiconductor substrate and including a blue filter selectively absorbing light in a blue wavelength region and a red filter selectively absorbing light in a red wavelength region, and the organic photoelectronic device on the color filter layer and selectively absorbing light in a green wavelength region.

The organic photoelectronic device may be a green photoelectronic device selectively absorbing light in a green wavelength region, and the image sensor may include the green photoelectronic device, a blue photoelectronic device selectively absorbing light in a blue wavelength region, and a red photoelectronic device selectively absorbing light in a red wavelength region are sequentially stacked.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
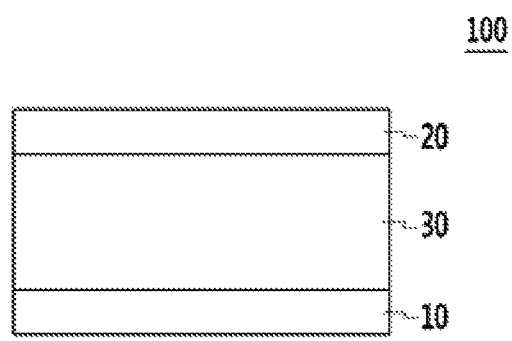
FIG. 1 is a cross-sectional view showing an organic photoelectronic device according to example embodiments.

Example embodiments will hereinafter be described in detail, and may be easily performed by those who have common knowledge in the related art. However, this disclosure may be embodied in many different forms and is not construed as limited to the example embodiments set forth herein.

As used herein, when a definition is not otherwise provided, the term "substituted" refers to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Parts having no relationship with the description are omitted for clarity, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Referring to the drawings, an organic photoelectronic device according to example embodiments is described.

FIG. 1 is a cross-sectional view of an organic photoelectronic device according to example embodiments.

Referring to FIG. 1, an organic photoelectronic device 100 according to example embodiments includes a first electrode 10 and a second electrode 20 facing each other, and an organic layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a thin monolayer or a multilayer. When one of the first electrode 10 and the second electrode 20 is a non-light-transmitting electrode, the first electrode 10 or the second electrode 20 may be made of, for example, an opaque conductor (e.g., aluminum (Al)).

The organic layer 30 includes a visible light-absorbing body absorbing light in the particular wavelength region of a visible ray and a charge buffer material substantially not absorbing light in the visible ray region but separating an exciton generated by the visible light-absorbing body into a hole and an electron.

The visible light-absorbing body may be an n-type semiconductor or a p-type semiconductor selectively absorbing light in a green wavelength region of the visible ray region and having a maximum absorption wavelength ($\lambda_{max}$) at about 500 nm to about 600 nm.

The visible light-absorbing body may be a compound represented by the following Chemical Formula 1.

[Chemical Formula 1]

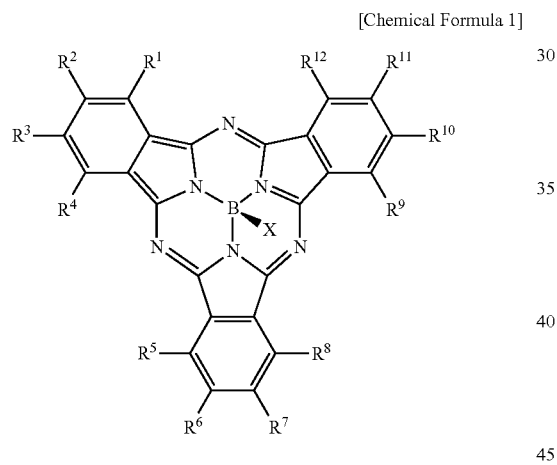

In the above Chemical Formula 1,
each of $R^1$ to $R^{12}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen atom, a halogen-containing group, and a combination thereof, and
X is an anion.

The compound represented by the above Chemical Formula 1 is a visible light-absorbing body having a maximum absorption wavelength ($\lambda_{max}$) at about 500 nm to about 600 nm, and has relatively high wavelength selectivity in a green wavelength region.

The compound represented by the above Chemical Formula 1 may function as an n-type semiconductor or a p-type semiconductor, and may be included as a visible light-absorbing body alone without a separate p-type semiconductor or a separate n-type semiconductor for forming a pn junction.

The compound represented by the above Chemical Formula 1 may be, for example, one of compounds represented by the following Chemical Formulae 1a to 1e, but is not limited thereto.

[Chemical Formula 1a]

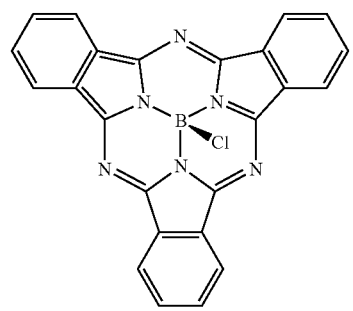

[Chemical Formula 1b]

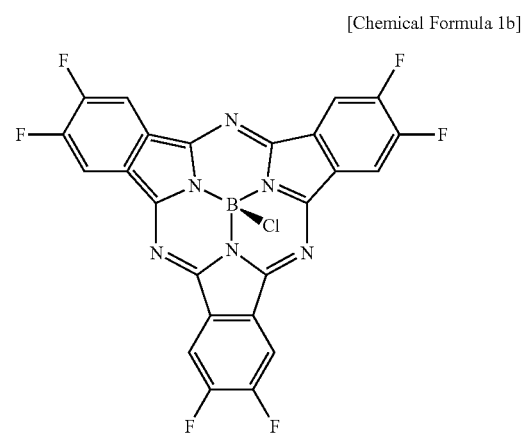

[Chemical Formula 1c]

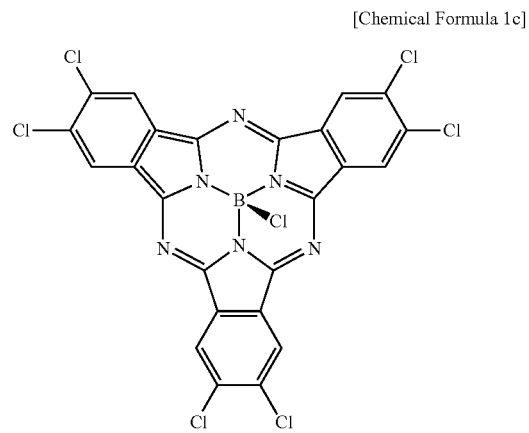

[Chemical Formula 1d]

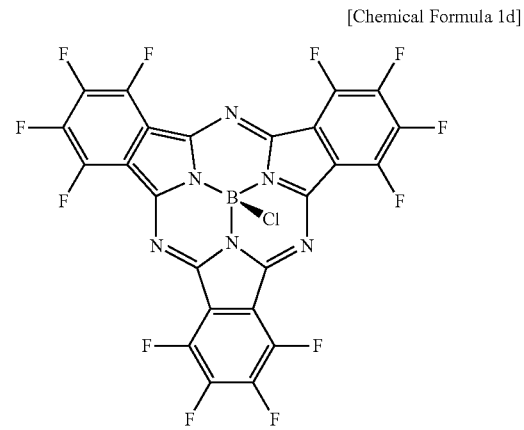

-continued

[Chemical Formula 1e]

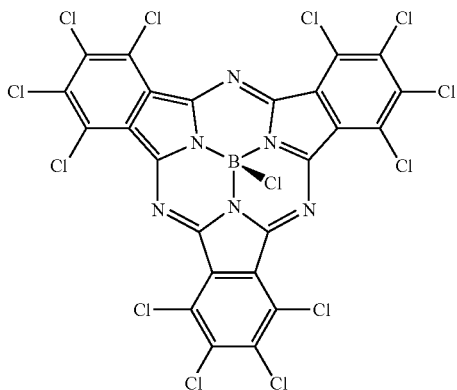

The charge buffer material does not substantially absorb visible light having a wavelength region of about 450 nm to about 800 nm and thus is not a visible light-absorbing body, and functions as an exciton quencher to separate an exciton generated by the visible light-absorbing body into a hole and an electron. The charge buffer material quenches excitons and separates them into holes and electrons, and thus may increase the number of holes transferring toward an anode and the number of electrons transferring toward a cathode, and thus improves efficiency of an organic photoelectronic device.

The charge buffer material may be at least one of a transparent hole buffer material and a transparent electron buffer material.

For example, the charge buffer material has an energy bandgap of greater than or equal to about 2.8 eV and thus transparency capable of passing light, and simultaneously has a HOMO level between the work function of the anode and the HOMO level of the compound represented by the Chemical Formula 1 and thus may be a hole buffer material capable of separating and transferring holes. Herein, the HOMO level indicates the absolute value of a HOMO level when a vacuum level is 0 eV.

The hole buffer material may have an energy bandgap of, for example, about 2.8 to about 4.0 eV.

The difference between the HOMO level of the hole buffer material and the HOMO level of the compound represented by the above Chemical Formula 1 may be, for example, about 0.01 to about 0.89 eV. The HOMO level of the hole buffer material may be, for example, greater than about 4.7 eV and less than about 5.6 eV.

The hole buffer material may be, for example, an amine-based compound, for example 4,4',4"-tris(N-(2-naphthyl)-N-phenyl-amino)-triphenylamine, N,N-diphenyl-N,N-bis(9-phenyl-9H-carbazol-3-yl)biphenyl-4,4'-diamine, N(diphenyl-4-yl)9,9-dimethyl-N-(4(9-phenyl-9H-carbazol-3-yl)phenyl)-9H-fluorene-2-amine, di-[4-(N,N-di-p-tolyl-amino)-phenyl]cyclohexane, 9,9-bis[4-(N,N-bis-biphenyl-4-yl -amino)phenyl]-9H-fluorene, and the like, but is not limited thereto.

For example, the charge buffer material has an energy bandgap of greater than or equal to about 2.8 eV, and thus may be an electron buffer material having transparency capable of passing light, and simultaneously has a LUMO level between the work function of the cathode and the LUMO level of the compound represented by the Chemical Formula 1. Herein, the LUMO level indicates the absolute value of a LUMO level when a vacuum level is 0 eV.

The electron buffer material may have an energy bandgap of, for example, about 2.8 to about 4.0 eV.

The difference between the LUMO level of the electron buffer material and the LUMO level of the compound represented by the Chemical Formula 1 may be, for example, about 0.01 to about 0.89 eV. The LUMO level of the electron buffer material may be, for example, greater than about 3.6 eV and less than 4.3 eV.

The electron buffer material may be, for example, carboxylic acid anhydride, for example 1,4,5,8-naphthalenetetracarboxylic dianhydride, but is not limited thereto.

For example, the charge buffer material may include both the hole buffer material and the electron buffer material.

The visible light-absorbing body and the charge buffer material may be included as a mixture in a monolayer, individually in a separate layer, or as a combination thereof.

Figure 2:
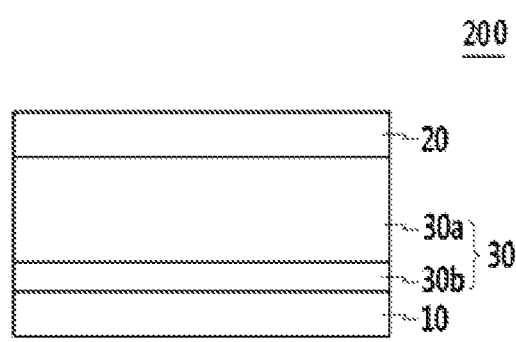
FIGS. 2 to 4 are cross-sectional views showing example embodiments of the organic photoelectronic device of FIG. 1.
Figure 3:
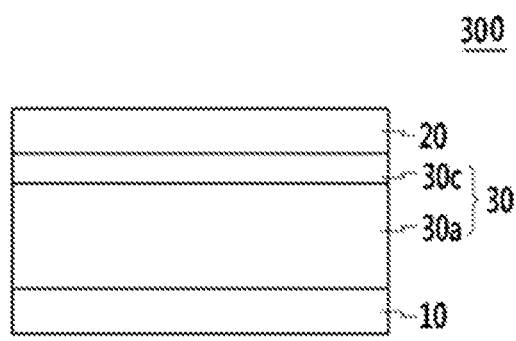
Figure 4:
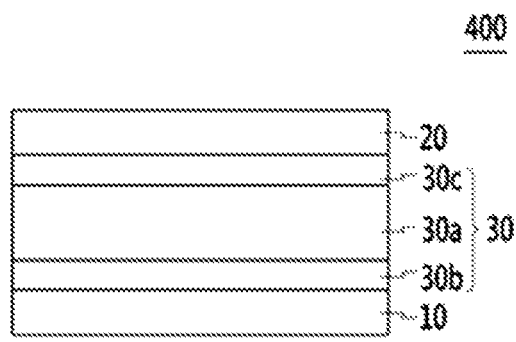
Figure 5:
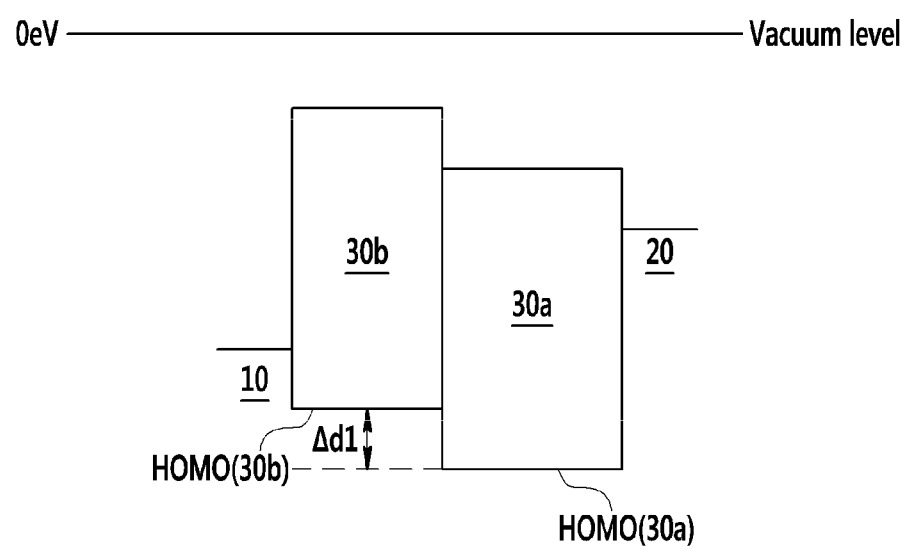
FIG. 5 is a diagram showing an energy level of the organic photoelectronic device of FIG. 2.
Figure 6:
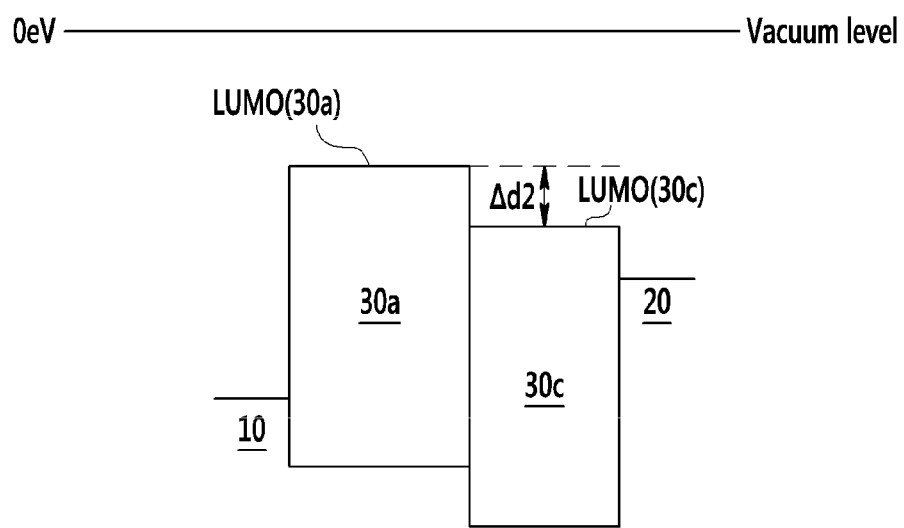
FIG. 6 is a diagram showing an energy level of the organic photoelectronic device of FIG. 3.

FIGS. 2 to 4 are cross-sectional views showing example embodiments of the organic photoelectronic device of FIG. 1, FIG. 5 is a diagram showing an energy level of the organic photoelectronic device of FIG. 2, and FIG. 6 is a diagram showing an energy level of the organic photoelectronic device of FIG. 3.

Referring to FIG. 2, the organic photoelectronic device 200 according to example embodiments includes a first electrode 10 and a second electrode 20 facing each other and an organic layer 30 interposed between the first electrode 10 and the second electrode 20, like the example embodiment illustrated in FIG. 1.

When the first electrode 10 is an anode and the second electrode 20 is an cathode, the organic layer 30 includes an active layer 30a including the compound represented by the above Chemical Formula 1 alone as a visible light-absorbing body, and a hole buffer layer 30b positioned on one side of the active layer 30a. The hole buffer layer 30b may include the above hole buffer material.

Referring to FIG. 5, the hole buffer layer 30b may have a HOMO level between the work function of the first electrode 10 as an anode and the HOMO level of the active layer 30a, and for example, a HOMO level difference Δd1 between HOMO levels of the hole buffer layer 30b and the active layer 30a in a range of about 0.01 to about 0.89 eV.

The active layer 30a may further include a hole buffer material other than the compound represented by the Chemical Formula 1. The hole buffer material included in the active layer 30a may have an energy bandgap of greater than or equal to about 2.8 eV and a HOMO level between the work function of the anode and the HOMO level of the compound represented by the Chemical Formula 1, and may be the same as or different from a hole buffer material included in the hole buffer layer 30b.

The hole buffer material included in the active layer 30a may be included in an amount of less than or equal to about 50 volume % based on the total weight of the active layer 30a. Within the range, the hole buffer material may be included in an amount of about 0.01 volume % to about 20 volume %, for example, about 0.01 volume % to about 10 volume %.

Referring to FIG. 3, the organic photoelectronic device 300 according to example embodiments includes a first electrode 10 and a second electrode 20 facing each other and an organic layer 30 interposed between the first electrode 10 and the second electrode 20, like the example embodiment illustrated in FIG. 2.

When the first electrode 10 is an anode and the second electrode 20 is an cathode, the organic layer 30 includes an active layer 30a including the compound represented by the above Chemical Formula 1 alone as a visible light-absorbing body, and an electron buffer layer 30c positioned on one side of the active layer 30a. The electron buffer layer 30c may include the above electron buffer material.

Referring to FIG. 6, the electron buffer layer 30c may have a LUMO level between the work function of the second electrode 20 as a cathode and the LUMO level of the active layer 30a, and for example, a LUMO level difference $\Delta d_2$ between LUMO levels of the electron buffer layer 30c and the active layer 30a may be in a range of about 0.01 to about 0.89 eV.

The active layer 30a may further include an electron buffer material besides the compound represented by the Chemical Formula 1. The electron buffer material of the active layer 30a may have an energy bandgap of greater than or equal to about 2.8 eV and a LUMO level between the work function of the cathode and the LUMO level of the compound represented by the Chemical Formula 1, and may be the same as or different from an electron buffer material included in the electron buffer layer 30c.

The electron buffer material of the active layer 30a may be included in an amount of less than or equal to about 50 volume % based on the active layer 30a. Within the range, the electron buffer material may be included in an amount of about 0.01 volume % to about 20 volume %, or about 0.01 volume % to 10 volume %.

Referring to FIG. 4, the organic photoelectronic device 400 according to example embodiments includes a first electrode 10 and a second electrode 20 facing each other and an organic layer 30 interposed between the first electrode 10 and the second electrode 20, like the example embodiment illustrated in FIG. 3.

When the first electrode 10 is an anode and the second electrode 20 is an cathode, the organic layer 30 includes an active layer 30a including the compound represented by the Chemical Formula 1 alone as a visible light-absorbing body, a hole buffer layer 30b positioned on one side of the active layer 30a, and an electron buffer layer 30c positioned on the other side of the active layer 30a. The hole buffer layer 30b may include the above hole buffer material, and the electron buffer layer 30c may include the above electron buffer material.

The active layer 30a may selectively absorb light at a maximum absorption wavelength ($\lambda_{max}$) in a green wavelength region of about 500 nm to about 600 nm.

The active layer 30a may show a light-absorption curve having a relatively small full width at half maximum (FWHM) ranging from about 50 nm to about 150 nm. Herein, the full width at half maximum (FWHM) indicates the width of a wavelength corresponding to a half of a maximum absorption point, and a small full width at half maximum (FWHM) indicates selective absorption of light in a narrow wavelength region and thus relatively high wavelength selectivity. The active layer 30a has a full width at half maximum (FWHM) within the range, and thus may increase selectivity in a green wavelength region.

The organic photoelectronic device 100 may internally produce excitons when light enters from the first electrode 10 and/or the second electrode 20, and the active layer 30a absorbs the light in a particular wavelength region. The excitons are separated into holes and electrons in the active layer 30a, the separated holes are transferred toward an anode, and one of the first electrode 10 and the second electrode 20, while the separated electrons are transferred toward a cathode, and the other of the first electrode 10 and the second electrode 20, so that a current may flow in an organic photoelectronic device.

The organic photoelectronic device may be applied to various fields, for example a solar cell, an image sensor, a photo-detector, a photo-sensor, and an organic light emitting diode (OLED), but is not limited thereto.

Hereinafter, an example of an image sensor including the organic photoelectronic device is described referring to drawings. As an example of an image sensor, an organic CMOS image sensor is described.

Figure 15:
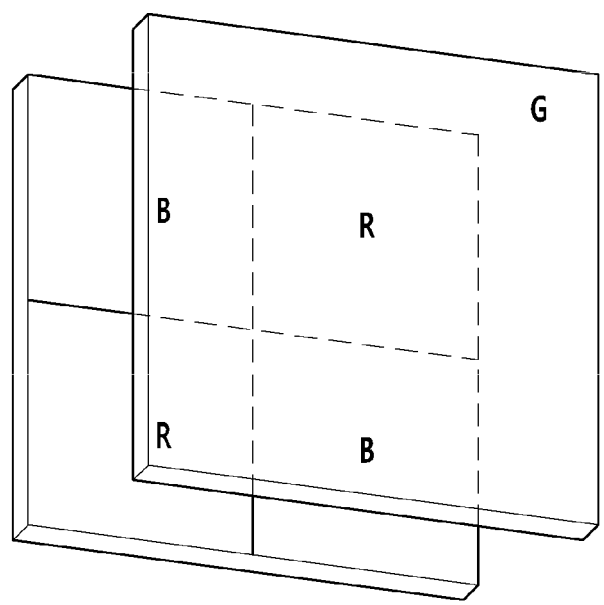
FIG. 15 is a top plan view schematically showing an organic CMOS image sensor according to example embodiments.
Figure 16:
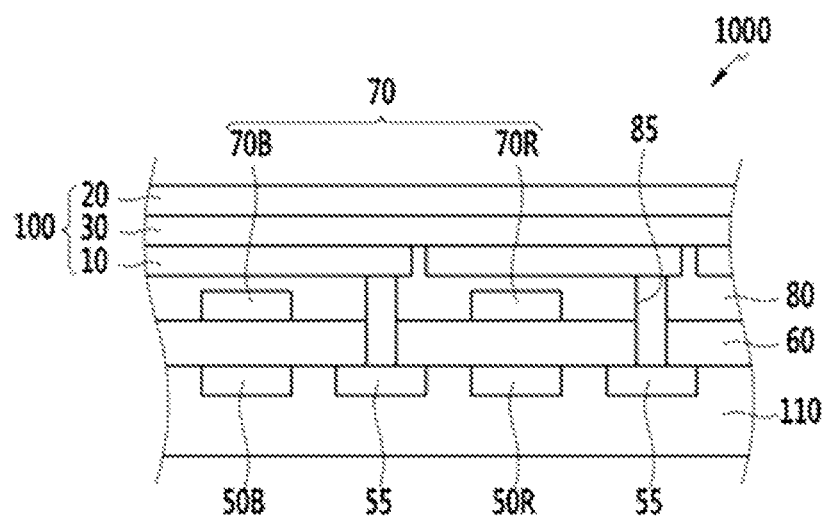
FIG. 16 is a cross-sectional view showing the organic CMOS image sensor of FIG. 15.

FIG. 15 is a top plan view schematically showing an organic CMOS image sensor according to example embodiments, and FIG. 16 is a cross-sectional view of the organic CMOS image sensor of FIG. 15.

Referring to FIGS. 15 and 16, an organic CMOS image sensor 1000 according to example embodiments includes a semiconductor substrate 110 integrated with photo-sensing devices 50B and 50R, a transmission transistor (not shown), and a charge storage 55, a lower insulation layer 60, a color filter 70, an upper insulation layer 80, and an organic photoelectronic device 100.

The semiconductor substrate 110 may be a silicon substrate, and the photo-sensing device 50, the transmission transistor (not shown), and the charge storage 55 are integrated therein. The photo-sensing device 50 may be a photo-diode.

The photo-sensing devices 50B and 50R, the transmission transistor, and/or the charge storage 55 may be integrated in each pixel. For example, as shown in the drawing, the photo-sensing devices 50B and 50R may include a blue pixel and a red pixel and the charge storage 55 may be included in a green pixel.

The photo-sensing devices 50B and 50R sense light, the sensed information may be transferred by a transmission transistor, and the charge storage 55 is electrically connected to the post-described organic photoelectronic device 100 and information of the charge storage 55 may be transferred by a transmission transistor.

Metal wires (not shown) and pads (not shown) are formed on the semiconductor substrate 110. In order to decrease signal delay, the metal wires and pads may be made of a metal having relatively low resistivity, for example, aluminum (Al), copper (Cu), silver (Ag), and alloys thereof, but is not limited thereto. However, the metal wire and pad may be positioned under the photo-sensing devices 50B and 50R without being limited to the structure.

The lower insulation layer 60 is formed on the metal wires and pads. The lower insulation layer 60 may be made of an inorganic insulating material (e.g., silicon oxide and/or silicon nitride), or a relatively low dielectric constant (low K) material (e.g., SiC, SiCOH, SiCO, and SiOF). The lower insulation layer 60 has a trench (not shown) exposing the charge storage 55. The trench may be filled with fillers.

A color filter layer 70 is formed on the lower insulation layer 60. The color filter layer 70 includes a blue filter 70B formed in the blue pixel, and a red filter 70R filled in the red pixel. In example embodiments, a green filter is not formed but a green filter may be formed.

The upper insulation layer 80 is formed on the color filter layer 70. The upper insulation layer 80 may eliminate a step caused by the color filter layer 70 and smooth the surface. The upper insulation layer 80 and the lower insulation layer 60 may include a contact hole (not shown) exposing a pad and a penetration hole 85 exposing a charge storage 55 of a green pixel.

The organic photoelectronic device 100 is formed on the upper insulation layer 80. The organic photoelectronic device 100 includes the first electrode 10, the organic layer 30, and the second electrode 20 as described above.

Both the first electrode 10 and the second electrode 20 may be transparent electrodes, the organic layer 30 may include a visible light-absorbing body absorbing light in a particular wavelength region of the visible ray region, and a charge buffer material substantially not absorbing light in the visible ray region but separating an exciton generated by the visible light-absorbing body into a hole and an electron as described above.

The visible light-absorbing body and the charge buffer material may be included as a mixture in a monolayer, individually in each separate layer, or as a combination thereof, and for example, the organic layer 30 may be an active layer 30a, a hole buffer layer 30b/the active layer 30a, the active layer 30a/an electron buffer layer 30c, or the hole buffer layer 30b/the active layer 30a/the electron buffer layer 30c as described above.

The active layer including the visible light-absorbing body may selectively absorb light in a green wavelength region.

When light enters from the second electrode 20, the light in a green wavelength region is mainly absorbed in the active layer and photoelectrically converted, while the light in the other wavelength region passes through the first electrode 10 and is sensed by a photo-sensing device 50.

As described above, the organic photoelectronic device selectively absorbing light in a green wavelength region is stacked, and thus may down-sized an image sensor and simultaneously increase sensitivity and decrease crosstalk.

Figure 17:
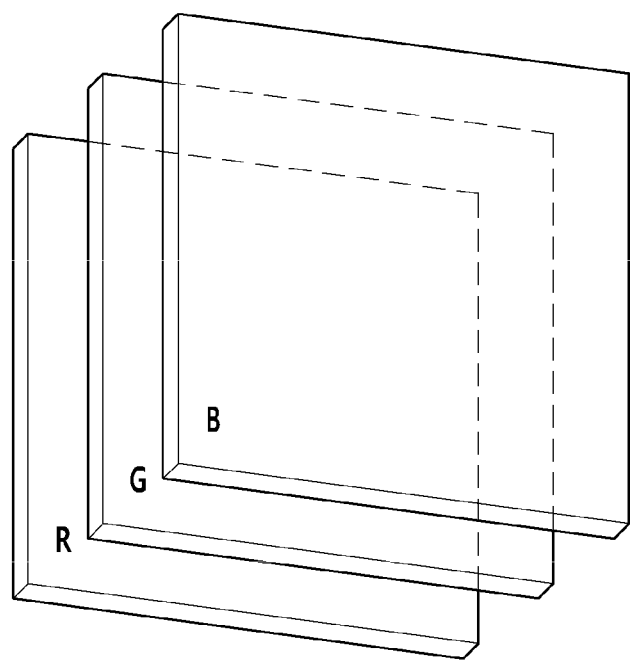
FIG. 17 is a top plan view schematically showing an organic CMOS image sensor according to example embodiments.

FIG. 17 is a top plan view schematically showing an organic CMOS image sensor according to example embodiments.

According to example embodiments, an organic CMOS image sensor has a structure in which a green photoelectronic device that selectively absorbs light in a green wavelength region, a blue photoelectronic device that selectively absorbs light in a blue wavelength region, and a red photoelectronic device that selectively absorbs light in a red wavelength region are stacked.

In the drawing, the red photoelectronic device, the green photoelectronic device, and the blue photoelectronic device are sequentially stacked, but example embodiments are not limited thereto, and the red, green, and blue photoelectronic devices may be stacked in various orders.

The green photoelectronic device may be the above organic photoelectronic device 100, the blue photoelectronic device may include electrodes facing each other, an active layer interposed therebetween, and including an organic material selectively absorbing light in a blue wavelength region, and the red photoelectronic device may include electrodes facing each other and an active layer interposed therebetween and including an organic material selectively absorbing light in a red wavelength region.

As described above, an organic photoelectronic device selectively absorbing light in a red wavelength region, an organic photoelectronic device selectively absorbing light in a green wavelength region, and an organic photoelectronic device selectively absorbing light in a blue wavelength region are stacked, and thus may further down-size an image sensor and simultaneously increase sensitivity and decrease crosstalk.

Hereinafter, the present disclosure is illustrated in more detail with reference to examples. However, these examples are exemplary, and the present disclosure is not limited thereto.

Manufacture of Organic Photoelectronic Device

EXAMPLE 1

ITO (a work function: 4.7 eV) is sputtered on a glass substrate to form an about 100 nm-thick anode, and BPAPF (9,9-bis[4-(N,N-bis-biphenyl-4-yl -amino)phenyl]-9H-fluorene) (LUMTEC) (HOMO: 5.56 eV, LUMO: 2.4 eV) is deposited to form a 50 nm-thick hole buffer layer. Subsequently, a compound represented by the following Chemical Formula 1a (HOMO: 5.6 eV. LUMO: 3.6 eV) is deposited on the hole buffer layer to form a 50 nm-thick active layer. Then, a 5 nm-thick auxiliary layer is formed on the active layer by depositing aluminum-doped molybdenum oxide (MoOx:Al, a doping amount of the Al: 50 wt %), and a 70 nm-thick cathode is formed on the auxiliary layer by thermally depositing aluminum (Al), manufacturing an organic photoelectronic device.

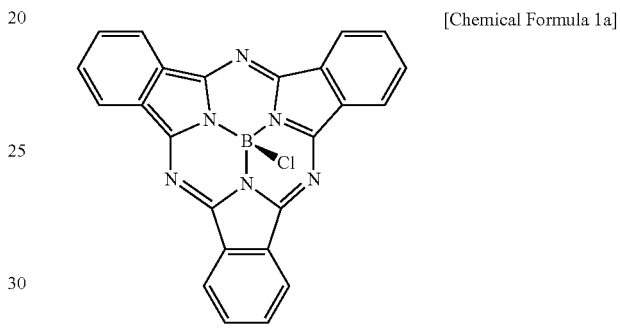

[Chemical Formula 1a]

EXAMPLE 2

An organic photoelectronic device is manufactured according to the same method as Example 1, except for using HT211 (N(diphenyl-4-yl)9,9-dimethyl-N-(4(9-phenyl-9H-carbazol-3-yl)phenyl)-9H-fluorene-2-amine) (HOMO: 5.4 eV, LUMO: 2.4 eV) instead of the BPAPF to form the hole buffer layer.

EXAMPLE 3

An organic photoelectronic device is manufactured according to the same method as Example 1, except for depositing HT01 (N,N-diphenyl-N,N-bis (9-phenyl-9H-carbazol-3-yl)biphenyl-4,4'-diamine) (HOMO: 5.2 eV, LUMO: 2.2 eV) instead of the BPAPF to form the hole buffer layer.

EXAMPLE 4

An organic photoelectronic device is manufactured according to the same method as Example 1, except for using HT211 (N(diphenyl-4-yl)9,9-dimethyl-N-(4(9-phenyl-9H-carbazol-3-yl)phenyl)-9H-fluorene-2-amine) (HOMO: 5.4 eV, LUMO: 2.4 eV) instead of the BPAPF to form the hole buffer layer and a mixture obtained by doping the compound represented by the above Chemical Formula 1a with 10 volume % of HT211 instead of the compound represented by the above Chemical Formula 1a to form the active layer.

EXAMPLE 5

An organic photoelectronic device is manufactured according to the same method as Example 1, except for using HT01 (N,N-diphenyl-N,N-bis(9-phenyl-9H-carbazol-3-yl)biphenyl-4,4'-diamine) (HOMO: 5.2 eV, LUMO: 2.2 eV) instead of the BPAPF to form the hole buffer layer and a mixture obtained by doping the compound represented by the above Chemical Formula 1a with 10 volume % of HT01 instead of the compound represented by the above Chemical Formula 1a.

EXAMPLE 6

Example 6 provides an inverse type of organic photoelectronic device, unlike Example 1.

ITO (a work function: 4.7 eV) is sputtered on a glass substrate to form an about 100 nm-thick cathode, and aluminum-doped molybdenum oxide (MoOx:Al, a doping amount of the Al: 50 wt %) is deposited to form a 5 nm-thick auxiliary layer. Subsequently, a compound represented by the Chemical Formula 1 a (HOMO: 5.6 eV. LUMO: 3.6 eV) is deposited to form a 50 nm-thick active layer. Then, HT211 (HOMO: 5.4 eV, LUMO: 2.4 eV) is deposited on the active layer to form a 50 nm-thick hole buffer layer. Then, aluminum (Al) is thermally deposited on the hole buffer layer to form an 80 nm-thick anode, manufacturing an organic photoelectronic device.

EXAMPLE 7

An organic photoelectronic device is manufactured according to the same method as Example 6, except for doping the compound represented by the Chemical Formula 1a with 10 volume % of HT211 (HOMO: 5.4 eV, LUMO: 2.4 eV) instead of the compound represented by the above Chemical Formula 1a to form the active layer.

EXAMPLE 8

An organic photoelectronic device is manufactured according to the same method as Example 6 except for doping the compound with 20 volume % of HT211 (HOMO: 5.4 eV, LUMO: 2.4 eV) instead of the compound represented by the above Chemical Formula 1a to form the active layer.

EXAMPLE 9

An organic photoelectronic device is manufactured according to the same method as Example 6, except for doping the compound represented by the above Chemical Formula 1a with 30 volume % of HT211 (HOMO: 5.4 eV, LUMO: 2.4 eV) instead of the compound represented by the above Chemical Formula 1a.

EXAMPLE 10

An organic photoelectronic device is manufactured according to the same method as Example 6, except for doping the compound represented by the above Chemical Formula 1a with 50 volume % of HT211 (HOMO: 5.4 eV, LUMO: 2.4 eV) instead of the compound represented by the Chemical Formula 1a to form the active layer.

EXAMPLE 11

ITO (a work function: 4.7 eV) is sputtered on a glass substrate to form an about 100 nm-thick anode, and a compound represented by the above Chemical Formula 1a (HOMO: 5.6 eV. LUMO: 3.6 eV) is deposited to be a 50 nm thick active layer. Subsequently, NTCDA (1,4,5,8-naphthalene tetracarboxylic dianhydride) is deposited on the active layer to be 20 nm thick to form an electron buffer layer. Then, aluminum-doped molybdenum oxide (MoOx:Al, a doping amount of the Al: 50 wt %) is deposited on the electron buffer layer to form a 5 nm-thick auxiliary layer, and aluminum (Al) is thermally deposited on the auxiliary layer to form a 70 nm-thick cathode, manufacturing an organic photoelectronic device.

Evaluation

Evaluation 1

Photoluminescence intensities of the organic photoelectronic devices of Examples 1 to 3 depending on a wavelength are evaluated.

The photoluminescence intensities are evaluated by using an F-7000 Fluorescence Spectrophotometer (Hitachi).

Figure 7:
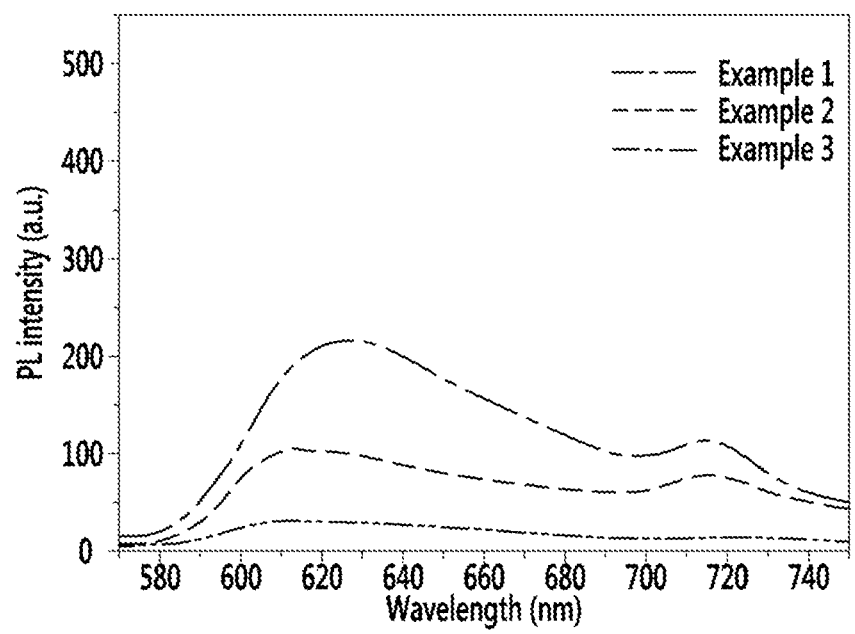
FIG. 7 is a graph showing photoluminescence intensities of the organic photoelectronic devices according to Examples 1 to 3 depending on a wavelength.

FIG. 7 is a graph showing photoluminescence intensities of the organic photoelectronic devices according to Examples 1 to 3 depending on a wavelength.

The photoluminescence intensities show a degree at which excitons are quenched and separated into holes and electrons, wherein the lower the photoluminescence intensities are, the better the excitons are separated.

Referring to FIG. 7, the organic photoelectronic devices according to Examples 1 to 3 show relatively low photoluminescence intensity, for example, a maximum photoluminescence intensity of lower than 300 a.u.

Accordingly, the organic photoelectronic devices according to Examples 1 to 3 are expected to have relatively high efficiency due to effective separation into holes and electrons.

Evaluation 2

External quantum efficiency (EQE) and full width at half maximum (FHWM) of the organic photoelectronic devices according to Examples 1 to 5 are evaluated.

The external quantum efficiency (EQE) is measured by using an IPCE measurement system (McScience Co., Ltd., Korea). First of all, the IPCE measurement system is calibrated by using a Si photodiode (Hamamatsu Photonics K.K., Japan) and mounted on the organic photoelectronic devices according to Examples 1 to 3, and their external quantum efficiencies are measured in a wavelength region range of about 350 to 800 nm.

The full width at half maximum (FHWM) is obtained by measuring width of a wavelength corresponding to a maximum absorption point in the external quantum efficiency graph.

Figure 8:
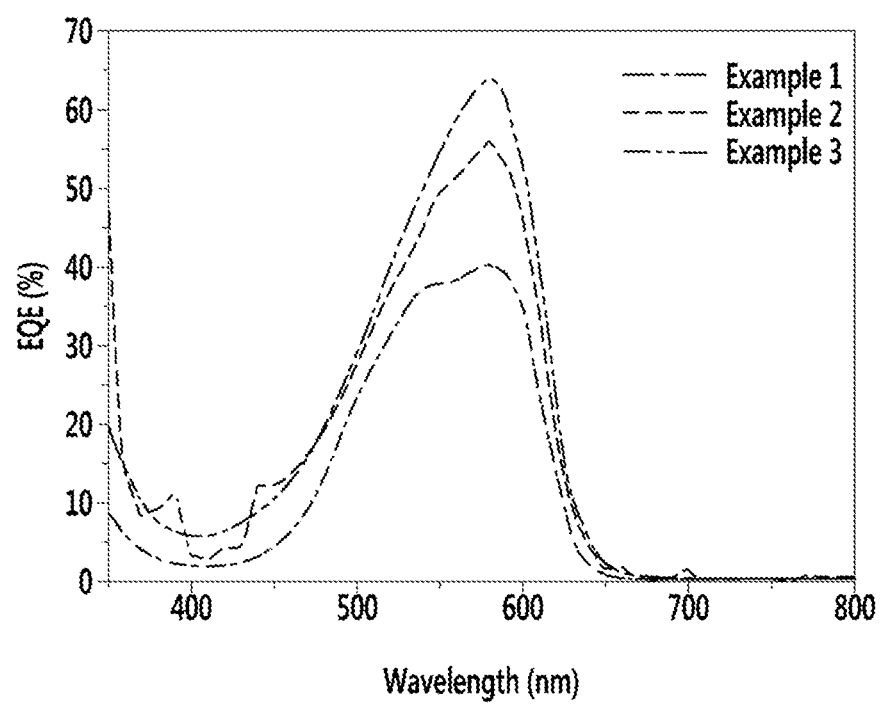
FIG. 8 is a graph showing external quantum efficiency (EQE) of the organic photoelectronic devices according to Examples 1 to 3 at 3 V depending on a wavelength.
Figure 9:
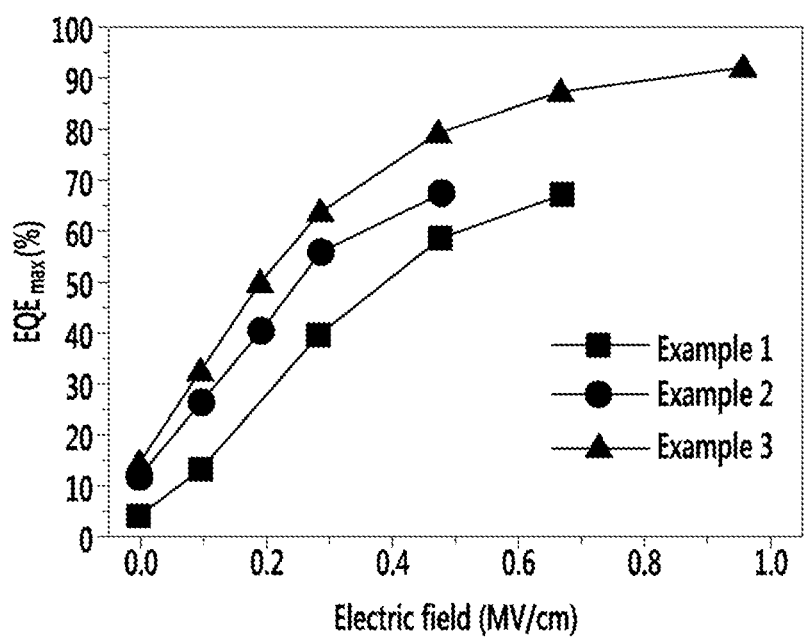
FIG. 9 is a graph showing external quantum efficiency of the organic photoelectronic devices according to Examples 1 to 3 at a maximum absorption wavelength ($\lambda_{max}$) depending on a voltage applied thereto.
Figure 10:
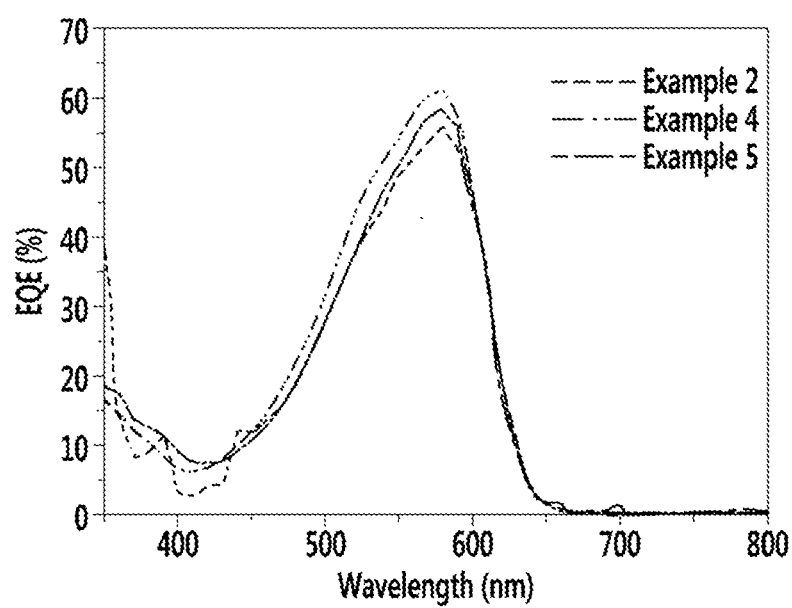
FIG. 10 is a graph showing external quantum efficiency (EQE) of the organic photoelectronic devices according to Examples 2, 4, and 5 at 3 V depending on a wavelength.
Figure 11:
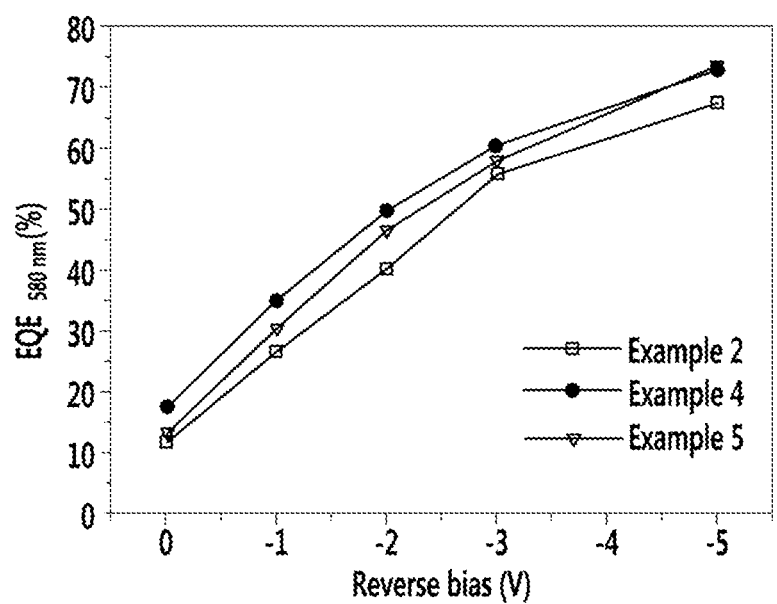
FIG. 11 is a graph showing external quantum efficiency of the organic photoelectronic devices according to Examples 2, 4, and 5 at a maximum absorption wavelength ($\lambda_{max}$) depending on a voltage applied thereto.
Figure 12:
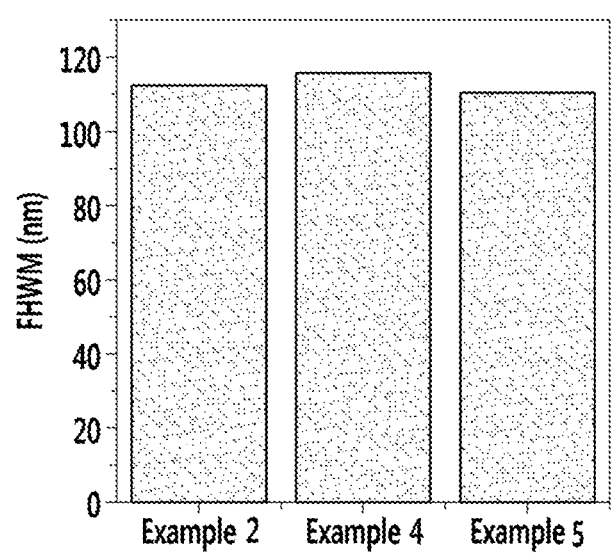
FIG. 12 is a graph showing a full width at half maximum of the organic photoelectronic devices according to Examples 2, 4, and 5.

FIG. 8 is a graph showing external quantum efficiency (EQE) of the organic photoelectronic devices according to Examples 1 to 3 at 3 V depending on a wavelength, FIG. 9 is a graph showing external quantum efficiency of the organic photoelectronic devices according to Examples 1 to 3 at a maximum absorption wavelength ($\lambda_{max}$) depending on a voltage, FIG. 10 is a graph showing external quantum efficiency (EQE) of the organic photoelectronic devices according to Examples 2, 4, and 5 at 3 V depending on a wavelength, FIG. 11 is a graph showing external quantum efficiency of the organic photoelectronic device according to Examples 2, 4, and 5 at a maximum absorption wavelength ($\lambda_{max}$) depending on an applied voltage, and FIG. 12 is a graph showing a full width at half maximum (FHWM) of the organic photoelectronic devices according to Examples 2, 4, and 5.

Referring to FIGS. 8 to 11, the organic photoelectronic devices according to Examples 1 to 5 show satisfactory external quantum efficiency (EQE) in a green wavelength region of about 500 nm to 600 nm.

Referring to FIG. 12, the organic photoelectronic devices according to Examples 2, 4, and 5 have a relatively small full width at half maximum (FHWM) of less than or equal to 150 nm. Accordingly, the organic photoelectronic devices have relatively high wavelength selectivity for light in a green wavelength region.

Evaluation 3

External quantum efficiency (EQE) of the organic photoelectronic devices according to Examples 6 to 10 is evaluated.

Figure 13:
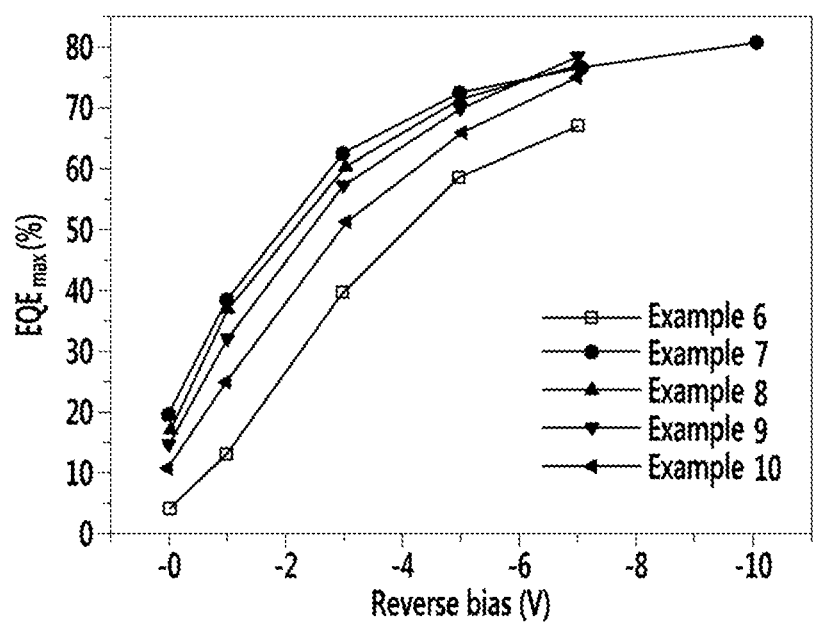
FIG. 13 is a graph showing external quantum efficiency of the organic photoelectronic devices according to Examples 6 to 10 at a maximum absorption wavelength ($\lambda_{max}$) depending on a reverse bias voltage.

FIG. 13 is a graph showing external quantum efficiency ($EQE_{max}$) of the organic photoelectronic devices according to Examples 6 to 10 at a maximum absorption wavelength ($\lambda_{max}$) depending on a reverse bias voltage.

Referring to FIG. 13, the organic photoelectronic devices according to Examples 6 to 10 show satisfactory external quantum efficiency (EQE) in a green wavelength region.

Evaluation 4

Photoluminescence intensity of the organic photoelectronic device according to Example 11 is evaluated.

Figure 14:
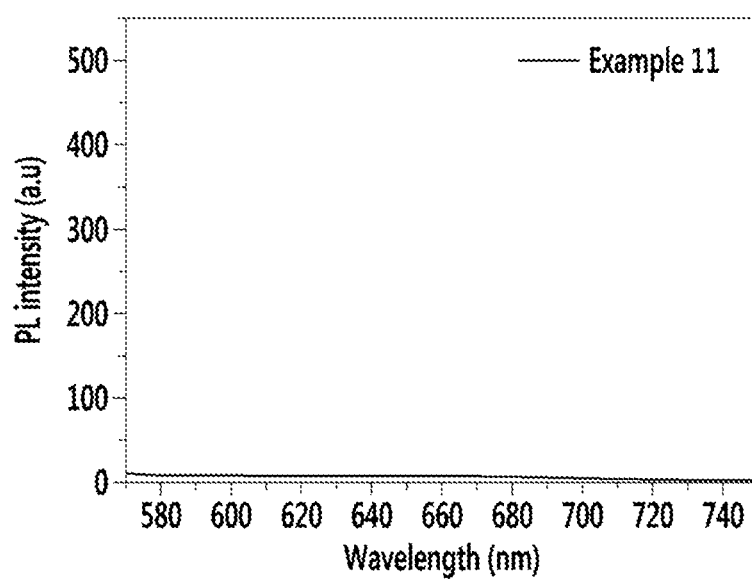
FIG. 14 is a graph showing photoluminescence intensity of the organic photoelectronic device according to Example 11 depending on a wavelength.

FIG. 14 is a graph showing photoluminescence intensity of the organic photoelectronic device according to Example 11 depending on a wavelength.

The photoluminescence intensity shows a degree at which excitons are quenched and separated into holes and electrons, and the lower the photoluminescence intensity is, the better the excitons are separated into holes and electrons.

Referring to FIG. 14, the organic photoelectronic device according to Example 11 shows relatively low photoluminescence intensity, for example, photoluminescence intensity near 0.

Accordingly, the organic photoelectronic device of Example 11 has relatively high efficiency due to effective separation into holes and electrons.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An organic photoelectronic device comprising:
   an anode and a cathode facing each other; and
   an organic layer between the anode and the cathode, the organic layer including,
      a compound represented by the following Chemical Formula 1 included as a visible light-absorbing body; and
      at least one of a hole buffer material having an energy bandgap of greater than or equal to about 2.8 eV and a HOMO level between a work function of the anode and a HOMO level of the compound represented by the following Chemical Formula 1, and an electron buffer material having an energy bandgap of greater than or equal to about 2.8 eV and a LUMO level between a work function of the cathode and a LUMO level of the compound represented by the following Chemical Formula 1:

[Chemical Formula 1]

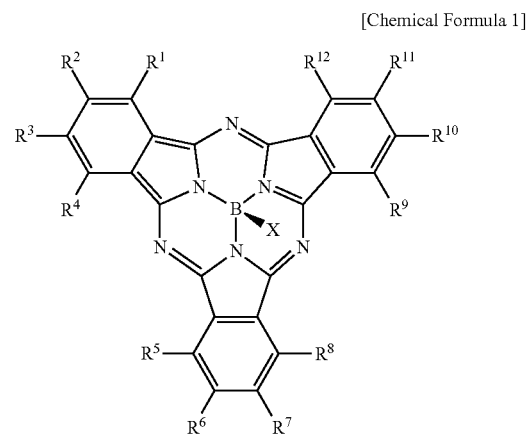

wherein, in the above Chemical Formula 1,
each of $R^1$ to $R^{12}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen atom, a halogen-containing group, and a combination thereof, and
X is an anion,
wherein
the compound represented by the above Chemical Formula 1 is configured to function as one of an n-type semiconductor and a p-type semiconductor; and
the organic photoelectronic device does not include a counterpart material for forming a pn junction with the compound.

2. The organic photoelectronic device of claim 1, wherein the at least one of the hole buffer material and the electron buffer material do not absorb visible light having a wavelength region of about 450 nm to about 800 nm.

3. The organic photoelectronic device of claim 1, wherein the organic layer further comprises:
   an active layer including the compound represented by the Chemical Formula 1; and
   a charge buffer layer on at least one side of the active layer, the charge buffer layer including a buffer layer including the at least one of the hole buffer material and the electron buffer material.

4. The organic photoelectronic device of claim 3, wherein the active layer further comprises the hole buffer material.

5. The organic photoelectronic device of claim 4, wherein the hole buffer material of the active layer is included in an amount of less than or equal to 50 volume % based on the active layer.

6. The organic photoelectronic device of claim 3, wherein the active layer further comprises the electron buffer material.

7. The organic photoelectronic device of claim 6, wherein the electron buffer material of the active layer is included in an amount of less than or equal to 50 volume % based on the active layer.

8. The organic photoelectronic device of claim 1, wherein the organic layer includes an active layer, the active layer including,
   the compound represented by the Chemical Formula 1, and
   at least one of the hole buffer material and the electron buffer material.

9. The organic photoelectronic device of claim 1, wherein
the at least one of the hole buffer material and the electron buffer material is the hole buffer material; and
the difference between the HOMO level of the hole buffer material and the HOMO level of the compound represented by the above Chemical Formula 1 is about 0.01 eV to about 0.89 eV.

10. The organic photoelectronic device of claim 1, wherein
the at least one of the hole buffer material and the electron buffer material is the hole buffer material; and
the HOMO level of the hole buffer material is greater than about 4.7 eV and less than about 5.6 eV.

11. The organic photoelectronic device of claim 1, wherein
the at least one of the hole buffer material and the electron buffer material is the electron buffer material; and
the difference between the LUMO level of the electron buffer material and the LUMO level of the compound represented by the Chemical Formula 1 is about 0.01 eV to about 0.89 eV.

12. The organic photoelectronic device of claim 1, wherein
the at least one of the hole buffer material and the electron buffer material is the electron buffer material; and
the LUMO level of the electron buffer material is greater than about 3.6 eV and less than 4.3 eV.

13. The organic photoelectronic device of claim 1, wherein the compound represented by the above Chemical Formula 1 is one of compounds represented by the following Chemical Formulae 1a to 1e:

[Chemical Formula 1a]

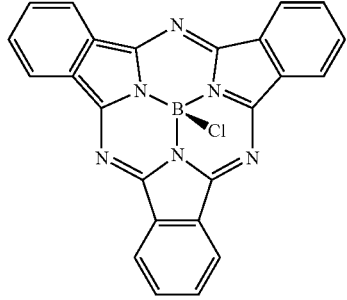

[Chemical Formula 1b]

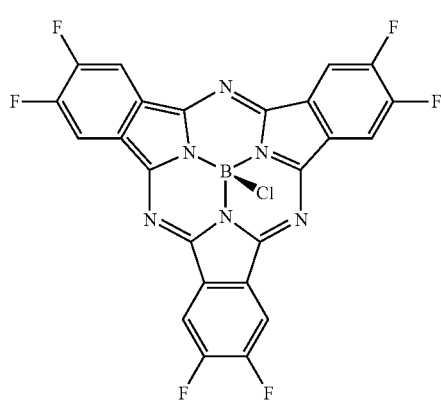

[Chemical Formula 1c]

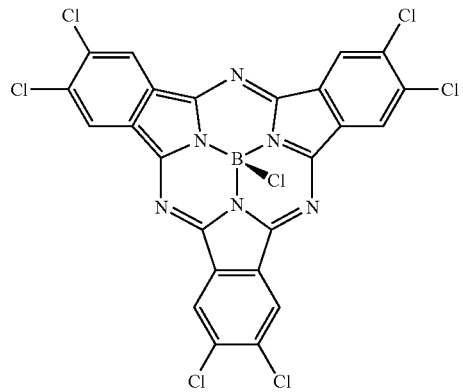

[Chemical Formula 1d]

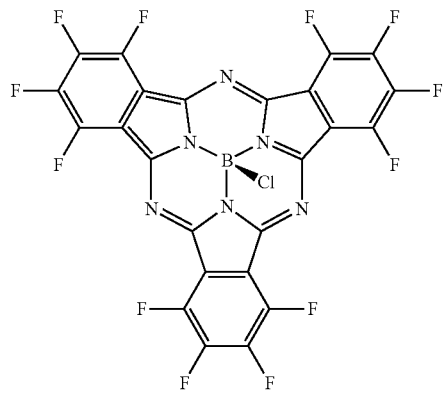

[Chemical Formula 1e]

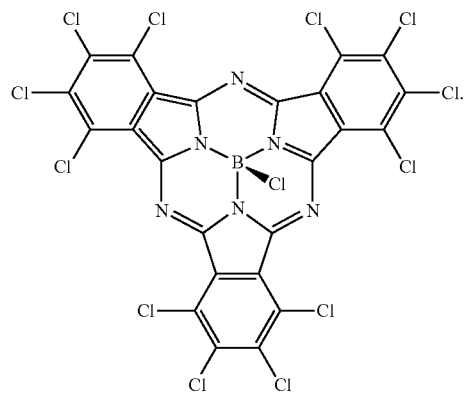

14. The organic photoelectronic device of claim 1, wherein the organic photoelectronic device selectively absorbs light of a green wavelength region.

15. The organic photoelectronic device of claim 1, wherein the organic photoelectronic device has a maximum absorption wavelength ($\lambda_{max}$) at about 500 nm to about 600 nm.

16. The organic photoelectronic device of claim 1, wherein the organic photoelectronic device shows a light-absorption curve having a full width at half maximum (FWHM) of about 50 nm to about 150 nm.

17. An image sensor comprising the organic photoelectronic device of claim 1.

18. The image sensor of claim 17, wherein the image sensor comprises:
a semiconductor substrate integrated with a plurality of first photo-sensing devices sensing light in a blue wavelength region and a plurality of second photo-sensing devices sensing light in a red wavelength region, a color filter layer on the semiconductor substrate, the color filter including a blue filter selectively absorbing light in the blue wavelength region and a red filter selectively absorbing light in the red wavelength region, and the organic photoelectronic device on the color filter layer, the organic photoelectronic device selectively absorbing light in a green wavelength region.

19. The image sensor of claim 17, wherein the organic photoelectronic device is a green photoelectronic device selectively absorbing light in a green wavelength region, and the green photoelectronic device, a blue photoelectronic device selectively absorbing light in a blue wavelength region, and a red photoelectronic device selectively absorbing light in a red wavelength region are sequentially stacked.

20. An image sensor comprising:

a semiconductor substrate integrated with a plurality of first photo-sensing devices sensing light in a blue wavelength region and a plurality of second photo-sensing devices sensing light in a red wavelength region, a color filter layer on the semiconductor substrate, the color filter including a blue filter selectively absorbing light in the blue wavelength region and a red filter selectively absorbing light in the red wavelength region, and an organic photoelectronic device on the color filter layer, the organic photoelectronic device selectively absorbing light in a green wavelength region, the organic photoelectronic device including, an anode and a cathode facing each other, and an organic layer between the anode and the cathode, the organic layer including, a compound represented by the following Chemical Formula 1 included as a visible light-absorbing body; and at least one of a hole buffer material having an energy bandgap of greater than or equal to about 2.8 eV and a HOMO level between a work function of the anode and a HOMO level of the compound represented by the following Chemical Formula 1, and an electron buffer material having an energy bandgap of greater than or equal to about 2.8 eV and a LUMO level between a work function of the cathode and a LUMO level of the compound represented by the following Chemical Formula 1:

[Chemical Formula 1]

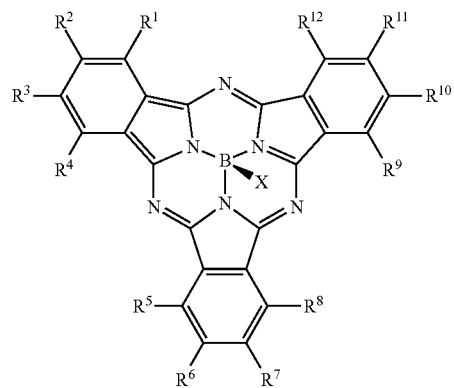

wherein, in the above Chemical Formula 1, each of $R^1$ to $R^{12}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen atom, a halogen-containing group, and a combination thereof, and X is an anion.

* * * * *